United States Patent [19]

Feldman et al.

[11] 3,999,544
[45] Dec. 28, 1976

[54] DISPOSABLE DIAPER HAVING PLEATED TAB FASTENER

[75] Inventors: Mark I. Feldman, Chicago; Ludwig Tritsch, Wilmette; Talivaldis Cepuritis, Kenilworth, all of Ill.

[73] Assignee: Johnson & Johnson, New Brunswick, N.J.

[22] Filed: Dec. 19, 1975

[21] Appl. No.: 642,285

[52] U.S. Cl. .................... 128/284; 128/287
[51] Int. Cl.² ............................ A61F 13/16
[58] Field of Search ................ 128/284, 287

[56] References Cited

UNITED STATES PATENTS

| | | | |
|---|---|---|---|
| 3,853,129 | 12/1974 | Kozak | 128/287 |
| 3,862,634 | 1/1975 | Small | 128/284 |
| 3,874,386 | 4/1975 | Kozak | 128/287 |

*Primary Examiner*—Aldrich F. Medbery

[57] ABSTRACT

A disposable diaper having a facing sheet defining a diaper inside surface for direction toward an infant and a backing sheet defining a diaper outside surface is provided with adhesive tabs comprising an integral elongated tape segment having a fixed end attached to the backing sheet at a location spaced inwardly from the edge of the backing sheet, an adhesive-coated free working end, and a pleated central segment. Release means is carried by the backing sheet between the edge thereof and the fixed end of the tab. The free end of the tab is movable from a storage position in which the central segment is pleated and extensibly folded and the free end is releasably adhered to the release means, to an extended working position in which the central segment is in an extended position and the free end is released from the release means and is available to secure the diaper about an infant.

15 Claims, 6 Drawing Figures

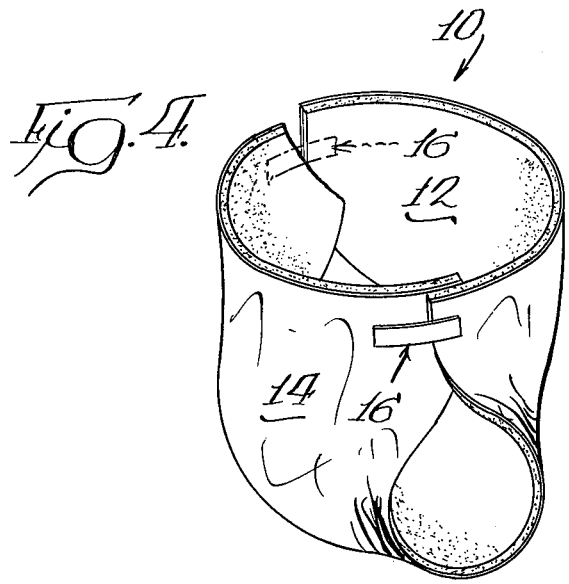
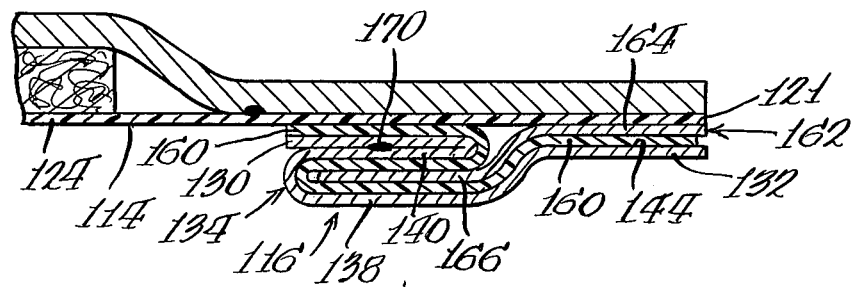
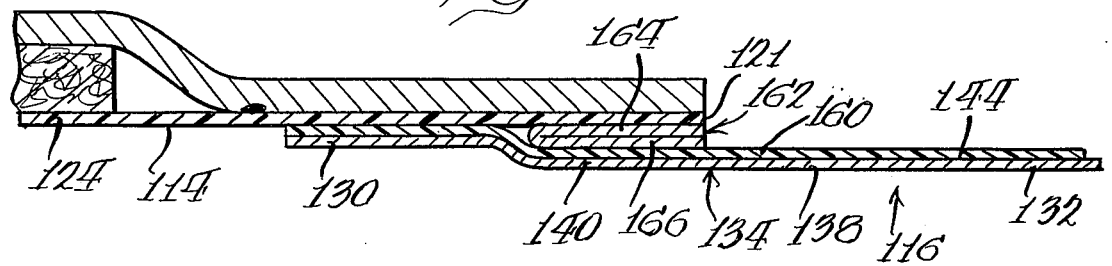

DISPOSABLE DIAPER HAVING PLEATED TAB FASTENER

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,646,937 to Gellert teaches a fastening tab which is provided with a release surface permanently bonded to the inside surface of the diaper. One of the drawbacks of the Gellert arrangement is that the release surface is on the inside surface of the diaper where it can possibly come into contact with an infant's tender skin when the diaper is used.

U.S. Pat. No. 3,750,669 to DeLuca shows a fastening tape provided with an adhesive end portion which extends beyond a cover strip for the tape and which is attached to a diaper inner covering or facing. However, such an adhesive end portion, when attached to a fibrous, non-woven facing fabric, may tear the facing fabric upon separation therefrom.

U.S. Pat. No. 3,776,234 to Hoey proposes to fold the tab over on itself at the diaper's edge and to adhesively attach a portion of the folded-over tab segment to an inwardly-folded margin of the diaper backing sheet in order to keep the tab flat against the diaper and thus from interfering with the manufacturing machinery and with the subsequent folding and packaging operations. This requires that the edge of the diaper backing sheet be folded over to present an attachment surface at the front or inside face of the diaper, and a relatively involved tab design is necessary for this purpose. Also, undesirable tearing of the diaper facing fabric may result if such a tab is inadvertently adhesively attached to the facing fabric of the diaper during manufacture.

U.S. Pat. No. 3,874,386 to Kozak discloses a tab fastener having a fixed end secured to a backing sheet, an opposite releasable end, and a middle segment carrying a release agent. The tab fastener is folded to superpose the releasable end segment and the middle segment over the fixed end, with the releasable end being releasably secured to the middle segment. Such a fold configuration restricts the distance at which the fixed end can be spaced from a longitudinal margin of the diaper and also requires that a substantial portion of the tab fastener itself by non-adhesive so as to accommodate the entire tacky area of the releasable free end. The non-adhesive portion, of course, is not available for securement.

SUMMARY OF THE INVENTION

According to the present invention, a pleated tab fastener for a disposable diaper comprising an integral elongated tape segment and having one end releasably attached to a diaper backing sheet is provided. The tab fastener comprises a tape segment having a fixed end permanently attached to a diaper backing sheet at a location spaced inwardly from longitudinal margin of the backing sheet, a pressure sensitive adhesive-coated free working end, and a pleated central segment. Release means is carried by the backing sheet and secured thereto between the fixed end of the tab and the longitudinal margin of the backing sheet. The free end is movable from a storage position in which the central segment is pleated and extensibly folded and the free end is releasably adhered to the release means, to an extended working position in which the central segment is in an extended condition and the free end is released from the release means and is available for securing the diaper about an infant.

In one embodiment, the portion of the pleat adjacent the free working end is provided with an adhesive coating, and the juxtaposed pleat portion, which is adjacent the fixed end, is provided with a second release means. When the tab is moved to the working position, both the free working end and the pleat portion adjacent the free working end are available for securing the diaper about an infant.

In another embodiment, an adhesive coating is provided on one face of substantially the entire tab, and the release means is a ribbon segment with a first end thereof attached to the backing sheet between the fixed end of the tab and the longitudinal margin of the backing sheet, and a second end received between contiguous pleat portions when the tab is in the storage position. The second end of the release means can be permanently attached to the pleat portion adjacent the fixed end. Both the free working end and the pleat portion adjacent the free working end are then available for securing the diaper about an infant when the tab is moved to the working position.

In both embodiments, substantially the entire portion of the tab that extends beyond the edge of the diaper in the extended position is adhesive-coated and available for securing the diaper about an infant.

The central pleat of the tape tab fasteners of the present invention can be tacked down to remain flat against the diaper when in the storage position or simply folded back over the fixed end or the releasably attached free working end so as not to interfere with the diaper manufacturing machinery and the subsequent folding and packaging operations. Additional features of this invention include a tape tab which is relatively easy to affix to the diaper, and which provides ample adhesive area for securement. Moreover, by attaching the fixed end of the tab away from the longitudinal margin of the diaper, stresses imposed on the tab as the infant moves about can be more widely distributed through the diaper.

BRIEF DESCRIPTION OF THE DRAWINGS

FIG. 4 is a perspective view of the diaper of FIG. 1 in a configuration assumed by the diaper when placed about an infant;

FIG. 5 is a fragmentary cross-sectional view, similar to FIG. 2, of another embodiment of the invention in a pleated folded back position; and FIG. 6 is a fragmentary cross-sectional view of the diaper of FIG. 5 in an extended position.

DESCRIPTION OF THE PREFERRED EMBODIMENTS

In the following description, two digit numerals are used to refer to the embodiment illustrated in FIGS. 1-4, and three digit numerals in the one hundred series are used to refer to the embodiment illustrated in FIGS. 5 and 6. The same last two digits in each numeral designate similar elements in the various embodiments.

Figure 1:
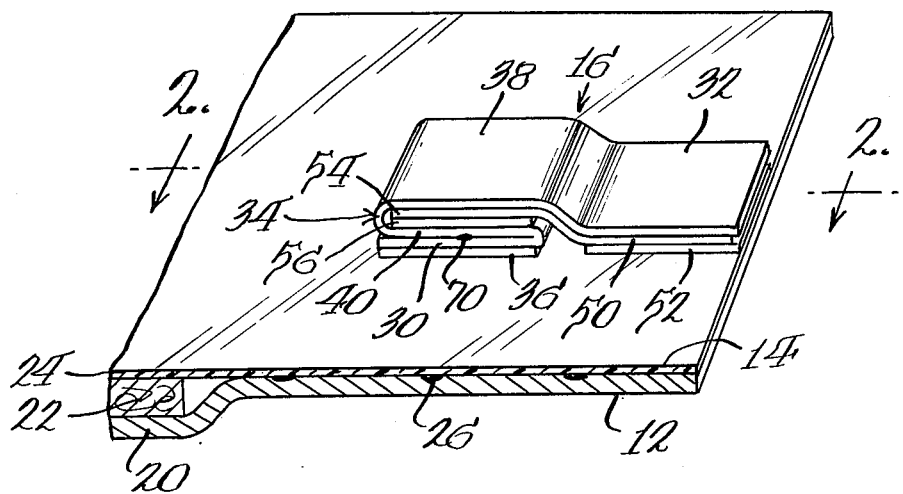
FIG. 1 is a fragmentary perspective view of an open unfolded diaper in accordance with the present invention.

Disposable tab 10, illustrated in FIGS. 1 and 4, is of substantially quadrilateral configuration and presents inside surface 12 for direction toward an infant and outside surface 14 for direction away from the infant. Adhesive to fastener means such as tabs 16 are attached to diaper 10 for securing diaper 10 about an infant. As described in greater detail below, tabs 16 are movable from a folded-over storage position illustrated in FIG. 2 to an extended working position which is illustrated in FIG. 3.

Figure 2:
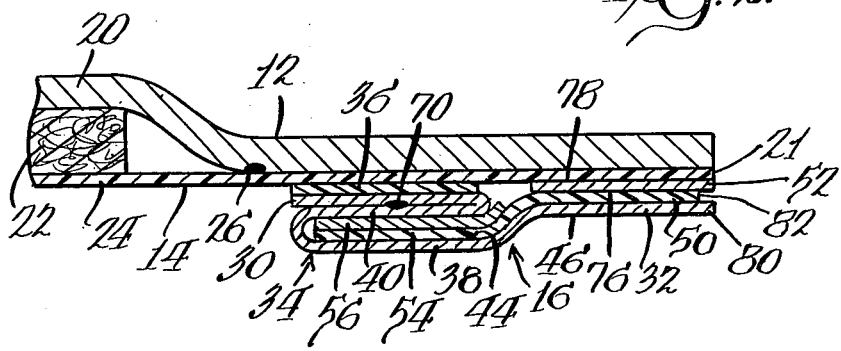
FIG. 2 is an enlarged fragmentary cross-sectional view of the diaper of FIG. 1 taken along plane 2—2.
Figure 3:
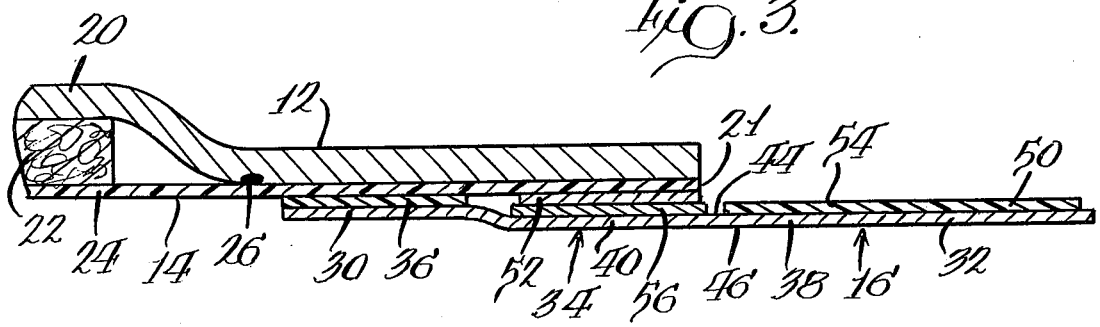
FIG. 3 is a fragmentary cross-sectional view similar to FIG. 2 but showing the tab fastener in an extended position.

Referring to FIGS. 1-3, diaper 10 comprises moisture-pervious facing sheet 20, defining diaper inside surface 12 and overlying moisture-retaining absorbent pad 22, and backing sheet 24 which is made of a moisture-impervious material and defines diaper outside surface 14. Absorbent pad 22 is somewhat smaller than backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to the backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 1, 2 and 3, adhesive tab 16 comprises an integral elongated tape segment having a fixed end 30, free working end 32 and a central segment 34 therebetween. Fixed end 30 has adhesive coating 36 on one face thereof permanently attaching tab 16 to backing sheet 20 at a location spaced inwardly from longitudinal margin 21 of the backing sheet. By attaching fixed end 30 away from the longitudinal margin of backing sheet 20, stresses imposed on tab 16 as the infant moves about can be more widely distributed through the diaper. Adhesive coating 36 for fixed end 30 can be a pressure-sensitive adhesive composition, a heat-activated or solvent-activated adhesive composition or the like.

Central segment 34 has a pleat which can be extensibly folded back over fixed end 30, as shown in FIGS. 1 and 2 when in storage position and can be extended to the working position illustrated in FIG. 3. The pleat includes a first pleat portion 38 adjacent to free end 32 and a second pleat portion 40 adjacent to fixed end 30 and which is juxtaposed to first pleat portion 38 when central segment 34 is pleated.

Tab 16 has an inner face 44 facing in the same direction as diaper inside surface 12 when tab 16 is in the extended working position of FIG. 3, and an opposite outer face 46. Pressure-sensitive adhesive coating 50 is provided on inside face 44 of free working end 32, faces in the same direction as diaper inside surface 12 when tab 16 is in the working position, and provides a securement means which can be moved from the storage position of FIG. 2 to the extended working position of FIG. 3 for fastening the diaper about an infant.

Release means 52 is provided and is carried on backing sheet 24 situated between longitudinal margin 21 and the location where the fixed end 30 of tab 16 is attached to the backing sheet. Release means 52 provides a release region facing in the same direction as diaper outside surface 14. When tab 16 is in the storage position of FIG. 2, adhesive coating 50 on free end 32 of tab 16 is releasably adhered to release means 52 which is substantially coextensive with adhesive coating 50.

Adhesive coating 36 on fixed end 30 and pressure-sensitive adhesive coating 50 on free end 32 preferably are positioned on the respective inner faces 44 thereof. In the embodiment shown in FIGS. 1-3, pressure-sensitive adhesive coating 54 is provided on inner face 44 of first pleat portion 38. Adhesive coatings 50 and 54 may comprise a continuous adhesive coating. A second release means 56 is provided on inner face 44 of the juxtaposed second pleat portion 40 so that adhesive-coated first pleat portion 38 is releasably adhered to second pleat portion 40 when tab 16 is in the storage position of FIG. 2. To prepare tab 16 for use, free end 32 of tab 16 can be grasped by a user, separated from first release means 52, and pulled outwardly to extend central segment 34 and separate first pleat portion 38 from second release means 56. Tab 16 thereby assumes the extended working position depicted in FIG. 3 wherein both free end 32 and first pleat portion 38 extend beyond the longitudinal margin 21 of backing sheet 20 and are available for securing the diaper about an infant.

In the embodiment illustrated in FIGS. 5 and 6, a continuous pressure-sensitive adhesive coating 160 is provided on the respective first faces 144 of free working end 132, first and second pleat portions 138 and 140, and fixed end 130 of tab 116. An integral elongated release means in the form of a release-coated ribbon 162 is provided with first end 164 permanently attached to backing sheet 124. When central segment 134 is pleated, as shown in FIG. 5, second end 166 of the ribbon is received between contiguous pleat portions 138, 140. Release coating on ribbon 162 provides a release region facing in the same direction as diaper outside surface 114. Second end 166 preferably is permanently attached by adhesive securement to second pleat portion 140, thereby providing further anchoring of tab 116 to backing sheet 124. First pleat portion 138 is releasably adhered to the release region on second end 166. Free end 132 can be grasped by a user, separated from first end 164 of release means 162, and pulled outwardly to separate first pleat portion 138 from second end 166 of release means 162. Thus extended tab 116 assumes the working position shown in FIG. 6 wherein free end 132 and first pleat portion 138 extend beyond the longitudinal margin 121 of backing sheet 120 and are available for securing the diaper about an infant while tab 116 is secured to diaper backing sheet by means of fixed end 130 as well as ribbon 162.

Referring now to both embodiments discussed hereinabove, spots of adhesive may be used to tack down the pleat in tabs 16 and 116. For example, adhesive spot 70 may be provided between fixed end 30 and second pleat portion 40 to releasably tack second pleat portion 40 to fixed end 30 when tab 16 is in the storage position. While adhesive spot 70 holds down the pleated tab in the storage position, the hold is readily broken when a user extends the tab to the working position.

As shown in FIG. 2, the release means may comprise a ribbon segment or release strip 52 provided with a release coated face 76 which provides the release region, and an adhesive coating on opposite face 78 by means of which release strip 52 is anchored to backing sheet 20. Alternatively, the release means may comprise a release coating, such as a silicone release compound, or the like printed onto the diaper outside surface 14 and substantially coextensive with adhesive coating 50 on free end 32 when tab 16 is in the pleated storage position.

It is desirable to provide a gripping means to facilitate grasping tab 16 to separate adhesive coating 50 on free end 32 of tab 16 from release means 52 preparatory to fastening the diaper about an infant. As depicted in FIG. 2, free end 32 can include projecting portion 80 which extends inwardly on diaper 10 beyond outermost margin or edge 82 of adhesive coating 50. The outwardly extending segment 80 provides a gripping means for separating adhesive coating 50 on tab 16 from release means 52.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coating 50 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75 to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, non-woven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a non-apertured material, such as a non-woven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web abut 0.001" thick. Another suitable material for this purpose is a polyethylene terephthalate web having a thickness of about 0.0005". Typical disposable diapers which can be fitted with tab-type adhesive fasteners described hereinabove are shown in U.S. Pat. No. 3,612,055 to Mesek et al. and in U.S Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means.

The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling free end 32 of tab 16 away from its temporary engagement with release means 52, exposing adhesive coating 50 which was releasably adhered to release means 52. The tabs are then pulled outwardly until the pleated central segment 34 is straightened to assume an extended position, whereupon tabs 16 are used to secure the diaper in the desired position by simply urging the pressure-sensitive adhesive surfaces in contact with the adjacent outer surface of the diaper. The applied diaper assumes the configuration illustrated in FIG. 4.

The foregoing description and the drawings are illustrative but are not to be taken as limiting. Still other variations and modifications are possible without departing from the spirit and scope of the present invention.

We claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:
   an integral elongated tape segment having a fixed end, a free working end, and an extensibly folded central segment having a pleat between said fixed end and said free working end, said fixed end being permanently attached to said backing sheet at a location spaced inwardly from a longitudinal margin of said backing sheet;
   a pressure-sensitive adhesive coating on one face of said free working end; and
   release means for adhesion of said one face of the free working end carried on said backing sheet between said location and said margin and providing a release region facing in the same direction as said diaper outside surface;
   said free end being movable from a storage position, in which the central segment is pleated and said free end is releasably adhered to said release region, to a working position in which the central segment is in an extended condition and said free end is released from said release means and is available for securing said diaper about an infant.

2. The disposable diaper as defined in claim 1 wherein said central segment is folded back over said fixed end and wherein a spot of adhesive is positioned between said fixed end and a pleat portion adjacent thereto to tack said adjacent pleat portion to said fixed end when said tape segment is in said storage position.

3. The disposable diaper as defined in claim 1 wherein said tape segment has an inner face facing in the same direction as said diaper inside surface when said tape segment is in said extended working position, and an opposite outer face, wherein a pressure-sensitive adhesive coating is provided on said fixed end on the inner face thereof, wherein said pressure-sensitive adhesive coating on said free end is positioned on the inner face thereof, and wherein a pressure-sensitive adhesive coating is provided on the inner face of a pleat portion adjacent to said free working end and is releasably adhered to a juxtaposed pleat portion when said tape segment is in said storage position; said tape segment being movable from said storage position to a working position in which said pressure-sensitive adhesive-coated pleat portion is also available for securing said diaper about an infant.

4. The disposable diaper as defined in claim 3 wherein a second release means is provided on the inner face of said juxtaposed pleat portion.

5. The disposable diaper as defined in claim 3 wherein said adhesive coatings on the inner faces of said free end and said adjacent pleat portion comprise a continuous adhesive coating on said first faces thereof.

6. The disposable diaper as defined in claim 3 wherein said free end and said adjacent pleat portion extend beyond said margin of said backing sheet when said tape segment is in said working position.

7. The disposable diaper as defined in claim 1 wherein said tape segment has an inner face facing in the same direction as said diaper inside surface when said tape segment is in said extended working position, and an opposite outer face, wherein a substantially continuous pressure-sensitive adhesive coating is provided covering said inner face of the tape segment, wherein said release means is a release-coated ribbon segment having a first end permanently attached to said backing sheet and a second end received between contiguous pleat portions when said central segment is pleated and providing a release region facing in the same direction as said diaper outside surface; said pleat portion adjacent to said free working end being releasably adhered to said release region on said second end of said release means when said tab is in storage position.

8. The disposable diaper as defined in claim 7 wherein said second end of said release means is permanently attached to the pleat portion juxtaposed to said adjacent pleat portion.

9. The disposable diaper as defined in claim 1 wherein said release means comprises a ribbon segment carried by said backing sheet and provided with a release coating substantially coextensive with said free end of said tape segment and facing in the same direction as said diaper outside surface.

10. The disposable diaper as defined in claim 1 wherein said release means is a release coating on a portion of said diaper outside surface.

11. The disposable diaper as defined in claim 10 wherein said release coating comprises a silicone release compound.

12. The disposable diaper as defined in claim 4 wherein said second release means comprises a ribbon segment carried by said juxtaposed pleat portion and provided with a release coating substantially coextensive with said pleat portion adjacent to the free working end and facing in the same direction as said diaper outside surface when said tape segment is in said working position.

13. The disposable diaper as defined in claim 4 wherein said second release means is a release coating on said juxtaposed pleat portion and faces in the same direction as said outside surface when said tape segment is in said working position.

14. The disposable diaper as defined in claim 12 wherein said release coating comprises a silicone release compound.

15. The disposable diaper as defined in claim 1 wherein a portion of said free end projects beyond the outermost edge of said adhesive coating carried by said free end, and wherein said projecting portion provides a gripping means for separating said tape segment from said release means when fastening said diaper about said infant.

* * * * *

UNITED STATES PATENT AND TRADEMARK OFFICE
CERTIFICATE OF CORRECTION

PATENT NO. : 3,999,544
DATED : December 28, 1976
INVENTOR(S) : Mark Feldman, Ludwig Tritsch, Talivaldis Cepuritis It is certified that error appears in the above-identified patent and that said Letters Patent are hereby corrected as shown below:

In Column 3, line 28, "Disposable tab 10" should read --- Disposable diaper 10 ---.

In Column 6, line 54, "abut" should read --- about ---.

In Column 8, Claim 7, line 40, "in storage position" should read --- in said storage position ---.

Signed and Sealed this

Third Day of May 1977

[SEAL]

Attest:

RUTH C. MASON
*Attesting Officer*

C. MARSHALL DANN
*Commissioner of Patents and Trademarks*